(12) United States Patent
Qiao et al.

(10) Patent No.: US 6,562,783 B2
(45) Date of Patent: May 13, 2003

(54) PHOSPHINYLMETHYL AND PHOSPHORYLMETHYL SUCCINIC AND GLUTAURIC ACID ANALOGS AS β-SECRETASE INHIBITORS

(75) Inventors: Lixin Qiao, Arlington, VA (US); René Etcheberrigaray, Columbia, MD (US)

(73) Assignee: Neurologic, Inc., Rockville, MD (US)

( * ) Notice: Subject to any disclaimer, the term of this patent is extended or adjusted under 35 U.S.C. 154(b) by 0 days.

(21) Appl. No.: 09/866,764

(22) Filed: May 30, 2001

(65) Prior Publication Data

US 2002/0187928 A1 Dec. 12, 2002

(51) Int. Cl.[7] .................. C07D 295/205; C07K 19/00; C07K 101/02; A61K 31/495; A61K 38/07
(52) U.S. Cl. .................. 514/7; 514/85; 530/331; 544/337
(58) Field of Search ................. 514/7, 85; 530/331; 544/337

(56) References Cited

FOREIGN PATENT DOCUMENTS

WO WO 99/33849 A1 * 7/1999
WO WO 00/64911 A1 * 11/2000

OTHER PUBLICATIONS

Burke, J.R. et al, Postgraduate Medicine, 106, 1999, pp. 85–96.*
Shoulson, I., Science, 282. 1998, 1072–1074.*

* cited by examiner

*Primary Examiner*—Mukund J. Shah
*Assistant Examiner*—Thomas McKenzie
(74) *Attorney, Agent, or Firm*—Hunton & Williams

(57) ABSTRACT

The invention provides a compound of formula (I):

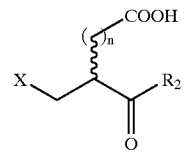

or salts or hydrates thereof, useful as beta-secretase inhibitors. The invention further relates to a method of reducing plaque formation, particularly useful in the treatment of Alzheimer's disease.

8 Claims, 5 Drawing Sheets

LQ β-4: R' = H;
LQ β-5: R' = iso-propyl;

15 R = Bn or isopropyl

Dose-Response of LQβ3 on sAPPα Secretion

PHOSPHINYLMETHYL AND PHOSPHORYLMETHYL SUCCINIC AND GLUTAURIC ACID ANALOGS AS β-SECRETASE INHIBITORS

FIELD OF THE INVENTION

The invention relates to phosphinylmethyl or phosphorylmethyl succinic and glutaric acid analogs designed to inhibit β-secretase in the metabolic processing of the amyloid precursor protein (APP). The invention also provides methods for the synthesis of phosphinylmethyl or phosphorylmethyl succinic and glutaric acid analogs, and further provides therapeutic methods for administration of the compounds for the treatment of plaque formation, especially in Alzheimer's disease.

BACKGROUND OF THE INVENTION

Alzheimer's disease (AD) affects approximately 5–15% of the U.S. population over age 65. This disease is frequently associated with individuals over the age of 60. Alzheimer's disease is the most frequent cause of institutionalization for long-term care. It is now estimated that 4.1 million Americans suffer from AD incurring $100 billion in U.S. health care costs per year.

Alzheimer's disease is characterized by the deposition of β-amyloid (Aβ) peptide in the extracellular compartment of the brain in the form of cognophilic amyloid angiopathy and amyloid plaques. (Small, D. H., Mclean, C. A, Alzheimer's disease and the amyloid β protein: what is the role of amyloid?, 73 *J. Neurochem* 443–49, 1999; Masliah, E., Role of amyloid precursor protein in the mechanisms of Neurodegeneration in Alzheimer's disease, 77 *Lab. Investig.* 197–209, 1997). Recent research on cellular and molecular aspects of Alzheimer's disease over the last two decades suggested that the metabolic fate of the amyloid precursor protein (APP) is one of the key factors in the pathogenesis of AD. (Lins, L., et al., Molecular determinants of the interaction between the C-terminal domain of Alzheimer's β-amyloid peptide and apolipoprotein E α-Helices, 73 *J. Neurochem.* 758–69, 1999; Selkoe, D. J., Normal and abnormal biology of the β-amyloid precursor protein, 17 *Annu. Rev. Neurosci.*, 489–517, 1994; Tanzi, R. E., et al., The gene defects responsible for familial Alzheimer's disease, 3 *Neurobiology of Disease* 159–68, 1996; Selkoe, D. J., Alzheimer's disease: genotypes, phenotype and treatments, 275 *Science* 630–31, 1997; Hardy, J. Amyloid, the presenilins and Alzheimer's disease, 20 *TINS* 154–159, 1997; Lendon, C. L., et al., Exploring the etiology of Alzheimer disease using molecular genetics, 277 *JAMA* 825–31, 1997).

Figure 1:
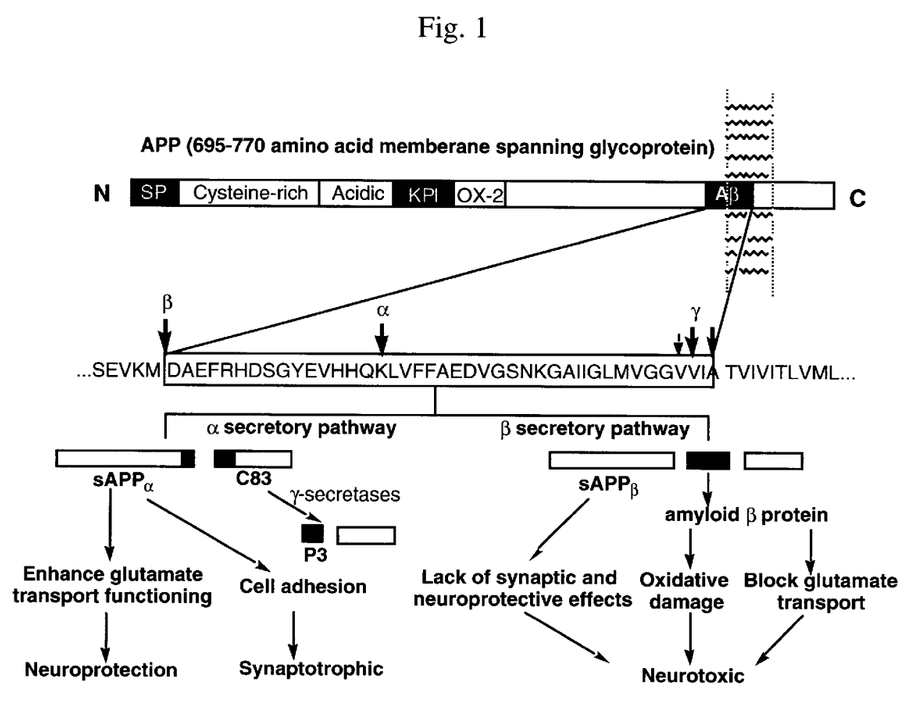
FIG. 1 is a diagram of primary structure of APP including an outline of the three secretase pathways and the mechanism for the generation of Aβ.

Amyloid precursor protein is a 695–770 amino acid membrane spanning glycoprotein, widely and constitutively expressed in the neurons and glial cells in peripheral tissues. Aβ, a 39–42 amino acid peptide, constitutes part of the ectodomain of APP and extends partly to the transmembrane domain. There are three secretory pathways involved in the APP processing. α-Secretase cleaves Lys16 and Leu17 of Aβ sequence giving rise to soluble APP (sAPP) (see FIG. 1). (Small, D. H., Mclean, C. A., Alzheimer's disease and the amyloid β protein: what is the role of amyloid?, 73 *J. Neurochem* 443–49, 1999; Masliah, E., Role of amyloid precursor protein in the mechanisms of Neurodegeneration in Alzheimer's disease, 77 *Lab. Investig.* 197–209, 1997). This pathway is non-amyloidogenic and to date, the products P3 and C83 are considered non-participants in AD pathology. Cleavage of APP by α-secretase produces a large soluble NH2-terminal fragment, sAPPα, and a 10-KD membrane-bound COOH terminal fragment C83. C83 can be further cleaved by one or more γ-secretases to release the nonpathogenic p3 peptide. (Skovronsky, D. M., et al., Protein kinase C-dependent α-secretase competes with β-secretase for cleavge of amyloid-β precursor protein in the trans-Golgi network, 274(4) *J. Biol. Chem.* 2568 -75, 2000; Jolly-Tornetta, C., Wolf, B. A., Regulation of amyloid protein (APP) secretion by protein kinase Cα in human Ntera 2 neurons (NT2N), 39 *Biochemistry* 7428–35, 2000).

Through the β-secretory pathway, Aβ is produced from the cleavage of APP at the N terminus of Aβ by β-secretase and cleavage at the C terminus of Aβ by γ-secretase. The extended forms of Aβ aggregate more readily and may seed amyloid fibril polymerization during the early stages of plaque formation. The Aβ accumulation is critical to AD as suggested by findings that mutations in several genes associated with familial AD (FAD) increase amyloidogenic Aβ production. (Selkoe, D. J., Alzheimer's disease: genotypes, phenotype, and treatments, 275 *Science* 630–31, 1997; Price, D. L., Sisodia, S. S., Mutant genes in familial Alzheimer's disease and transgenic models, 21 *Annu. Rev. Neurosci.* 479–505, 1998).

A growing list of evidence has demonstrated that enhanced sAPP secretion is associated with diminished Aβ production, suggesting that the secretory processing of APP to sAPPα reduces the formation of potentially amyloidogenic derivatives. Most of the experimental evidence suggests that α and β secretases compete for the same pool of APP. (Skovronsky, D. M., et al., Protein kinase C-dependent α-secretase competes with β-secretase for cleavage of amyloid-β precursor protein in the trans-Golgi network, 275(4) *J. Biol. Chem.* 2568–75, 2000; Jolly-Tornetta, C., Wolf, B. A., Regulation of amyloid protein (APP) secretion by protein kinase Cα in human Ntera 2 neurons (NT2N), 39 *Biochemistry* 7428–35, 2000). Therefore, the relative ratio of amyloidogenic vs. nonamyloidogenic products could be altered by regulating the activity of either secretase.

Additionally, presenilin 1 was also identified recently to control the hydrolysis at the intramembrane γ-secretase site and has been postulated to be itself the responsible protease. (Wolfe, M. S. et al., Are presenilins intramembrane-cleaving proteases? Implication for the molecular mechanism of Alzheimer's Disease, 38 *Biochemistry* 11223–30, 1999; Selkoe, D. J., Wolfe, M. S., In search of γ-secretase; Presenilin at the cutting edge, 97 *Proc. Natl. Acad. Sci.* 5690–92, 2000; Li, Y-M. et al., Presenilin 1 is linked with γ-secretase activity in the detergent solubilized state, 97 *Proc. Natl. Acad. Sci.* 6138–43, 2000; De Strooper, B. et al., Deficiency of presenilin-1 inhibits the normal cleavage of amyloid precursor protein, 391 *Nature* 387–90, 1998; Wolfe, M. S. et al., Two transmembrane aspartates in presenilin-1 required for presenilin endoproteolysis and γ-secretase activity, 398 *Nature* 513–17, 1999; De Strooper, B. et al., A presenilin-1-dependent γ-secretase-like protease mediates release of Notch intracellular domain, 398 *Nature* 518–22, 1999; Kimberly, W. T. et al., The transmembrane aspartates in presenilin 1 and 2 are obligatory for γ-secretase activity and amyloid γ-protein generation, 275 *J. Biol. Chem.* 3173–78, 2000). Although several γ-secretase inhibitors have been reported, (Rishton, G. M. et al., Fenchylamine sulfonamide inhibitors of amyloid β peptide production by the γ-secretase proteolytic pathway: Potential small-molecule therapeutic agents for the treatment of Alzheimer's disease, 43 *J. Med. Chem.* 2297–99, 2000; Seiffert, D. et al., Presenilin-1 and 2 are molecular targets for γ-secretase inhibitors, *J. Biol.*

Chem. (in press); Li, Y.-M. et al., Photoactivated γ-secretase inhibitors directed to the active site covalently label presenilin 1, 405 Nature 689–94, 2000; Wolfe, M. S. et al., Peptidomimetic probes and molecular modeling suggest that Alzheimer's γ-secretase is an intramembrane-cleaving aspartyl protease, 38 Biochem. 4720–27, 1999; Wolfe, M. S. et al., A substrate-based difluoro ketone selectively inhibits Alzheimer's γ-secretase activity, 41 J. Med Chem. 6–9, 1998) the processing of APP by β-secretase is thought to be the rate-determining step in Aβ production. Therefore, β-secretase inhibitor emerges as a preferred therapeutic target in the treatment of Alzheimer's disease.

More recently, significant efforts have been devoted towards the identification of the β protease (Selkoe, D. J., Translating cell biology into therapeutic advances in Alzheimer's disease, 399 Nature 23–31, 1999; Vassar, R., et al., β-Secreatase cleavage of Alzheimer's amyloid precursor protein by the transmembrane aspartic protease BACE, 286 Science 735–41, 1999; Hussain, I., et al., Identification of a novel aspartic protease (Asp2) as β-secretase, 14 Mole. Cell. Neurosci. 419–27, 1999; Yan, R., et al., Membrane-anchored aspartyl protease with Alzheimer's disease β-secretase activity, 402 Nature 533–37, 1999; Sinha, S., et al., Purification and cloning of amyloid precursor protein β-secretase from human brain, 402 Nature 537–40, 1999; Lin, X., et al., Human aspartic protease memapsin 2 cleaves the β-secretase site of β-amyloid precursor protein, 97 Proc. Natl. Acad. Sci. 1456–60, 2000) so design and synthesis of β-secretases inhibitors become possible. A JACS communication appeared as the first report on the peptidyl β-secretase inhibitor. (Ghosh, A. K. et al., Design of potent inhibitors for human brain memapsin 2 (β-secretase), 122 J. Am. Chem. Soc. 3522–23, 2000).

Nevertheless, the peptidyl compounds exhibit problems with instability, low bioavailability, and poor pharmacological profiles. There is a need in the field of the invention for pseudo- and/or non-peptidyl potent and selective inhibitors that represent promising features of β-secretase inhibitors. The invention fulfills these needs and more, as will become apparent to one of skill in the art upon reading the following disclosure.

SUMMARY OF THE INVENTION

The invention provides a compound of formula (I):

or salts or hydrates thereof;
wherein n is 1 or 2;
wherein X is a phosphinylmethyl or phosphorylmethyl derivative of the formula (II):

wherein $R_1$ is H, OH, R, OR, SR, $NR_2$, $(CH_2)_mC(O)R$, $(CH_2)_mCOOR$, $(CH_2)_mP(O)(OR)_2$, $(CH_2)_mS(O)R$, or $(CH_2)_mSO_2R$; wherein each R is independently H, $(C_1–C_{22})$ alkyl, $(C_6–C_{10})$aryl, $(C_3–C_8)$cycloalkyl, $(C_2–C_{22})$alkenyl, $(C_5–C_8)$cycloalkenyl, $(C_7–C_{32})$aralkyl, $(C_7–C_{32})$alkylaryl, $(C_9–C_{32})$aralkenyl, or $(C_9–C_{32})$alkenylaryl; and where m is 1 to 5;
wherein $R_2$ is H, R, OR, SR, $NR_2$, $(CH_2)_mC(O)R$, $(CH_2)_m COOR$, $(CH_2)_mP(O)(OR)_2$, $(CH_2)_mS(O)R$, or $(CH_2)_mSO_2R$ with the proviso that $R_2$ is not OH;
wherein each R is independently H, $(C_1–C_{22})$alkyl, $(C_6–C_{10})$ aryl, $(C_3–C_8)$cycloalkyl, $(C_2–C_{22})$alkenyl, $(C_5–C_8)$ cycloalkenyl, $(C_7–C_{32})$aralkyl, $(C_7–C_{32})$alkylaryl, $(C_9–C_{32})$ aralkenyl, $(C_9–C_{32})$alkenylaryl, a dipeptide; a tripeptide; a heterocycle, or a derivative of said heterocycles,
where m is 1 to 5.

In one aspect, the invention provides pseudo- and/or non-peptidyl agents as β-secretase inhibitors. These inhibitors decrease the β-amyloid available for plaque formation.

The invention additionally provides agents for the treatment of various diseases associated with β-amyloid plaques, especially but not limited to the treatment of neurological diseases, for example, Alzheimer's disease.

The invention further provides libraries of phosphinylmethyl ($R_1$ is a C-linked substituent as defined above) and/or phosphorylmethyl ($R_1$ is OR) succinic acid derivatives (n=1) in which the succinoyl moiety is constant while various substitutents as given above are permitted at position $R_2$. Thus, in one embodiment, a phosphorylmethyl succinoyl core is attached to a plurality of $R_2$ groups, producing a class of compounds herein termed LQ-β1 and LQ-β2 series. Similarly, a phosphinylmethyl succinoyl core produces a library herein termed LQ-β3 series including LQ-β4 and LQ-β5 derivatives.

The invention further provides libraries of phosphinylmethyl ($R_1$ is a C-linked substituent as defined above) and/or phosphorylmethyl ($R_1$ is OR) glutaric acid derivatives (n=2) in which the moiety is constant while various substitutents as given above are permitted at position $R_2$. Thus, in one embodiment, a phosphorylmethyl core is attached to a plurality of $R_2$ groups, producing a class of compounds herein termed LQ-β1 and LQ-β2 series. Similarly, a phosphinylmethyl core produces a library herein termed LQ-β3 series including LQ-β4 and LQ-β5 derivatives.

The invention further provides compositions comprising phosphinylmethyl and/or phosphorylmethyl succinic and glutaric acid derivatives, or their salts, or their hydrates in a pharmaceutically acceptable carrier. In further embodiments, methods are provided for treatment of a subject having an over expression of β-amyloid (for example a subject with Alzheimer's disease-like symptoms), in which an effective amount of the aforementioned composition is administered to the subject.

The invention in another aspect provides methods for preventing or reducing the progress of plaque formation in which the cell is contacted with an effective amount of the aforementioned phosphinylmethyl and/or phosphorylmethyl succinic and glutaric acid derivatives. This will prove especially useful in diseases such as Alzheimer's disease.

In still a further aspect, the invention provides a method for inhibiting β-secretase, in which the protease is contacted with an effective amount of the aforementioned phosphinylmethyl and/or phosphorylmethyl succinic and glutaric acid derivatives. The instant invention provides numerous advantages over known compounds, such as lack of peptide characters and easy scale-up. In particular, the LQ-βseries compounds are superior to previously published peptidyl β-secretase inhibitor in that either phosphinyl or phosphoryl moiety preclude the chirality problem, which makes it easier for synthesis. These and other advantages will become apparent to those of skill in the art upon reading the following detailed description.

In another aspect, the invention the invention provides pseudo- and/or non-peptidyl agents for increasing the α-secretase pathway activity.

DETAILED DESCRIPTION OF THE INVENTION

The invention provides a compound of formula (I):

or salts or hydrates thereof;
wherein n is 1 or 2;
wherein X is a phosphinylmethyl or phosphorylmethyl derivative of the formula (II):

wherein $R_1$ is H, OH, R, OR, SR, $NR_2$, $(CH_2)_mC(O)R$, $(CH_2)_mCOOR$, $(CH_2)_mP(O)(OR)_2$, $(CH_2)_mS(O)R$, or $(CH_2)_mSO_2R$; wherein each R is independently H, $(C_1-C_{22})$ alkyl, $(C_6-C_{10})$aryl, $(C_3-C_8)$cycloalkyl, $(C_2-C_{22})$alkenyl, $(C_5-C_8)$cycloalkenyl, $(C_7-C_{32})$aralkyl, $(C_7-C_{32})$alkylaryl, $(C_9-C_{32})$aralkenyl, or $(C_9-C_{32})$alkenylaryl; and where m is 1 to 5;
wherein $R_2$ is H, R, OR, SR, $NR_2$, $(CH_2)_mC(O)R$, $(CH_2)_m$ COOR, $(CH_2)_mP(O)(OR)_2$, $(CH_2)_mS(O)R$, or $(CH_2)_mSO_2R$ with the proviso that $R_2$ is not OH;
wherein each R is independently H, $(C_1-C_{22})$alkyl, $(C_6-C_{10})$ aryl, $(C_3-C_8)$cycloalkyl, $(C_2-C_{22})$alkenyl, $(C_5-C_8)$ cycloalkenyl, $(C_7-C_{32})$aralkyl, $(C_7-C_{32})$alkylaryl, $(C_9-C_{32})$ aralkenyl, $(C_9-C_{32})$alkenylaryl, a dipeptide; a tripeptide; a heterocycle, or a derivative of said heterocycles,
where m is 1 to 5.

It will be appreciated by those skilled in the art that compounds of the invention having one or more chiral center(s) may exist in and be isolated in optically active and racemic forms. Some compounds may exhibit polymorphism. It is to be understood that the invention encompasses any racemic, optically-active, polymorphic, or stereoisomeric form, or mixtures thereof, of a compound of the invention, which possesses the properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase), or using other tests which are well known in the art.

Specific and preferred values listed below for radicals, substituents, and ranges, are for illustration only; they do not exclude other defined values or other values within defined ranges for the radicals and substituents.

$(C_1-C_{22})$alkyl includes linear and branched saturated alkyl groups. For example, C4 alkyl includes butyl, isobutyl and sec-butyl.

$(C_2-C_{22})$alkenyl includes linear and branched groups containing one or more double bonds.

Cycloalkyls, preferably $(C_3-C_8)$cycloalkyls including but not limited to cyclopropyl, cyclobutyl, cyclopentyl, cyclohexyl, cycloheptyl, or cyclooctyl.

Aryls, preferably, $(C_6-C_{10})$aryls including but not limited to phenyl, indenyl, 5,6,7,8-tetrahydronaphthyl, or naphthyl.

Heterocycles including but not limited to pyrrole, furan, thiophene, imidazole, oxazole, thiazole, pyrazole, 3-pyrolidine, pyridine, purine, quinoline, isoquinoline, and carbazole; and dervatives of said heterocylcles.

Mode of Administration and Pharmaceutical Compositions.

The compounds of the invention provide libraries of phosphinylmethyl ($R_1$ is a C-linked substituent as defined above) or phosphorylmethyl ($R_1$ is OR) succinic acid derivatives (n=1) in which the succinoyl moiety is constant while various substitutents as given above are permitted at position $R_2$. Thus, in one embodiment, a phosphorylmethyl succinoyl core is attached to a plurality of $R_2$ groups, producing a class of compounds herein termed LQ-β1 and LQ-β2 series. Similarly, a phosphinylmethyl succinoyl core produces a library herein termed LQ-β3 series including LQ-β4 and LQ-β5 derivatives.

The compounds of the invention also provides libraries of phosphinylmethyl ($R_1$ is a C-linked substituent as defined above) or phosphorylmethyl ($R_1$ is OR) glutaric acid derivatives (n=2) in which the moiety is constant while various substitutents as given above are permitted at position $R_2$. Thus, in one embodiment, a phosphorylmethyl core is attached to a plurality of $R_2$ groups, producing a class of compounds herein termed LQ-β1 and LQ-β2 series. Similarly, a phosphinylmethyl core produces a library herein termed LQ-β3 series including LQ-β4 and LQ-β5 derivatives.

The compounds of the invention include all hydrates and salts that can be prepared by those of skill in the art. Under conditions where the compounds of the invention are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion.

Alkali metal (for example, sodium, potassium or lithium) or alkaline earth metal (for example calcium) salts of carboxylic acids can also be made.

The compounds of the invention can be formulated as pharmaceutical compositions and administered to a subject, such as a human subject, rodent or primate, in a variety of forms adapted to the chosen route of administration, e.g., orally or parenterally, through nasal spray, by intravenous, intramuscular, topical or subcutaneous routes.

Thus, the compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or other suitable solvent, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as necessary, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula (I) in a liquid composition, such as a lotion, will be from about 0.1–25 wt %, preferably from about 0.5–10 wt %. The concentration in a semi-solid or solid composition such as a gel or a powder will be about 0.1–5 wt %, preferably about 0.5–2.5 wt %.

Accordingly, the invention includes a pharmaceutical composition comprising a compound as described above, or a pharmaceutically acceptable salt thereof, in combination with a pharmaceutically acceptable carrier. Pharmaceutical compositions adapted for oral, topical or parenteral administration, comprising an amount of one or more compounds effective to treat a mammalian cell proliferative disorder, are also included.

The nature and use of the invention is further illustrated, and will be better understood, by reference to the following example.

EXAMPLE 4-(2-Carboxymethyl-3-phosphono-propionyl)-piperazine-1-carboxylic acid 2-phenoxy-ethyl ester (LQ β-1)

Synthesis

Figure 2:
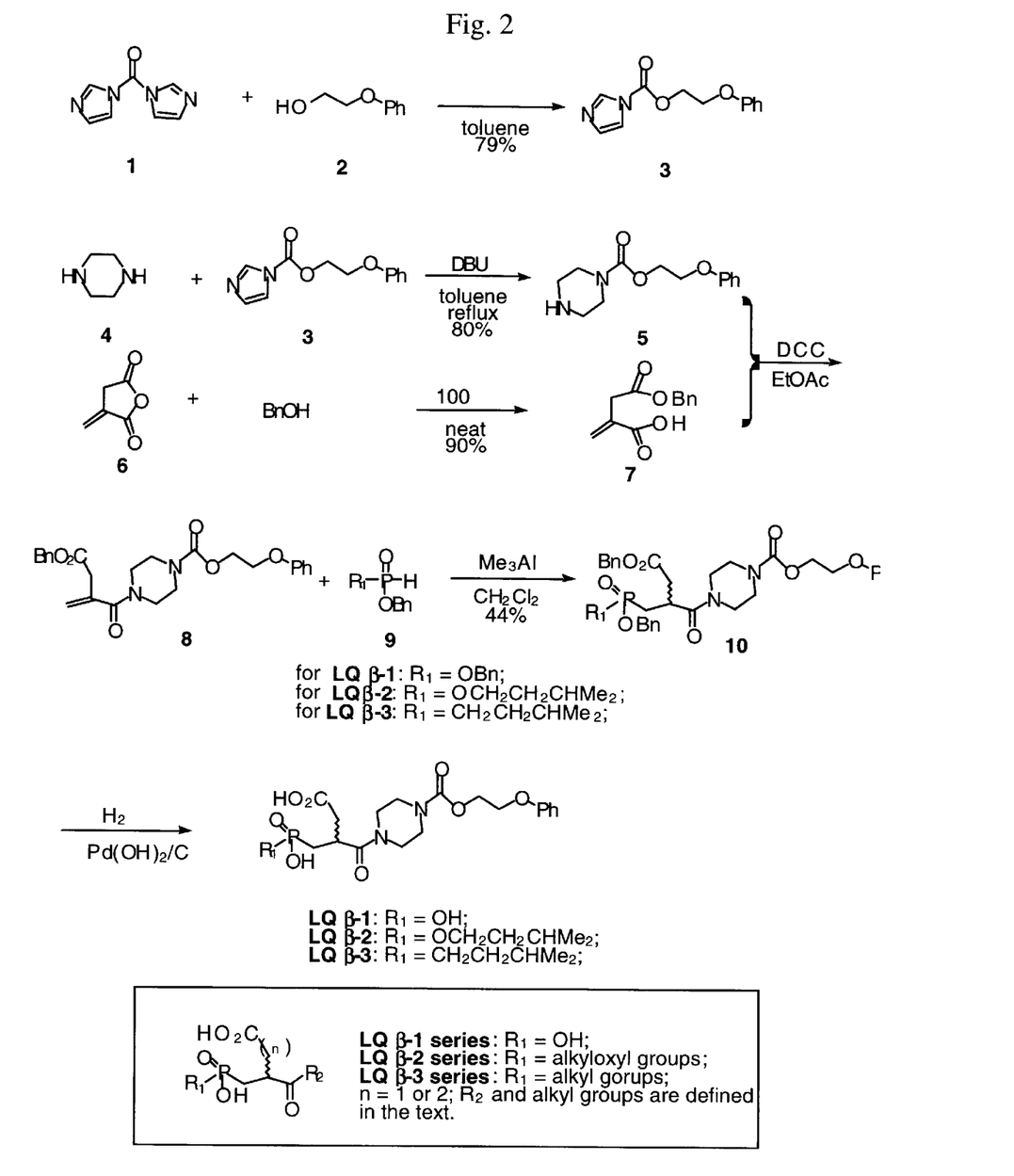
FIG. 2 is a schematic outline of the synthesis of phosphorylmethyl succinic and glutaric acid derivatives (LQ β-1 and LQ β-2 series) and phosphinylmethyl succinic and glutaric acid derivatives (LQ β-3 series).

In this example, the synthetic method for compound of the LQ β-1 series is described. It is also suitable for preparation of compounds in the LQ β-2 and LQ β-3 series, with appropriate phosphoryl and phosphinyl reagents. Referring now to FIG. 2, treatment of 1,1'-carbonyldiimidazole (1) with the same equivalent of 2-phenoxyethanol (2) gave rise to carbamate (3) in 79% yield. The immidazole group in compound (3) was then substituted by piperazine under basic condition affording carbamate (5). Meanwhile, itaconic anhydride was alcoholyzed with benzyl alcohol furnishing monoester (7) selectively. Subsequent condensation of carbamate (5) and itaconic monoester (7) with dehydrant DCC provided pseudo-aspartic/linkage/C-terminal (8). Next, Lewis acid catalyzed nucleophilic conjugate addition of phosphite (9) to compound (8) produced the fully protected target molecule. (Jackson, P. F., et al., Design, synthesis, and biological activity of a potent inhibitor of te neuropeptidase N-acetylated α-linked acidic dipeptidease 39 *J. Med. Chem.* 619–22, 1996; Nan, F. et al., Dual function glutamate-related ligands: Discovery of a novel, potent inhibitor of glutamate carboxypeptidase II possessing mGluR3 agonist activity, 43 *J. Med. Chem.* 772–74, 2000). At this stage, careful purification must be carried out to avoid any impurity getting into next step. Eventually, hydrogenolysis of all benzyl groups afforded desired inhibitor LQ-β1. The first compound LQ-β1 is a phosphonic acid, with a very hydrophilic pseudo-N terminal. Since small size and hydrophobicity are extremely important for penetrating the blood brain barrier, compounds of the LQ-β2 series were synthesized with the purpose of increasing lipophilicity. The phosphinate derivatived of the LQ-β3 series accomplished the modification at the pseudo N-terminal part. With the feedback from bioassay the better mimic, phosphinate, was chosen as the N-terminus mimic.

Figure 3:
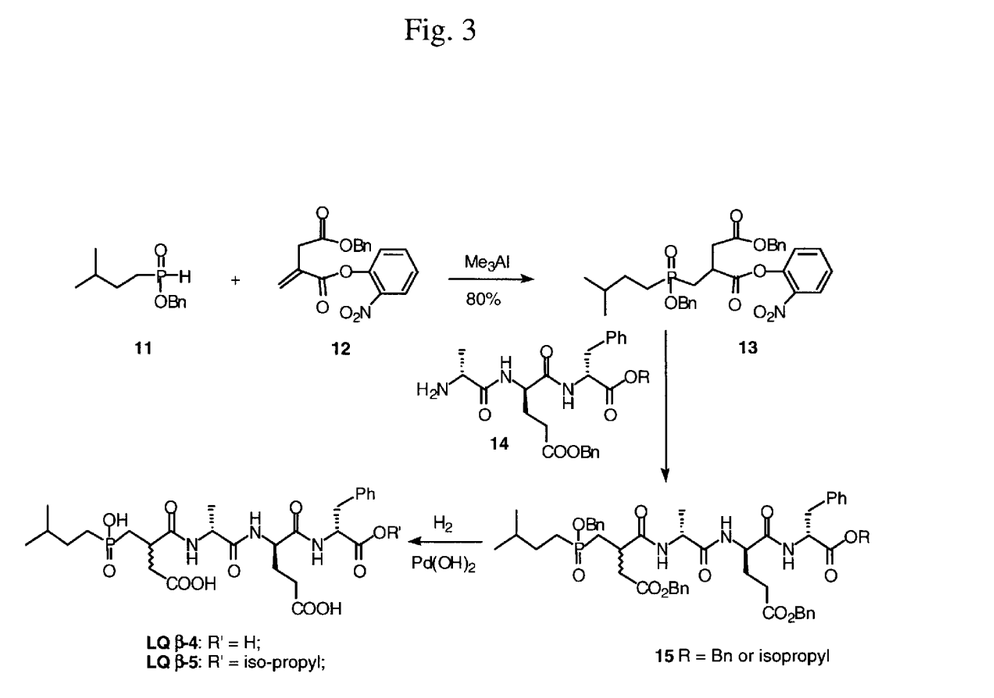
FIG. 3 shows the structures of phosphinylmethyl succinic and glutaric acid derivatives LQ β-4, and LQ β-5 from the LQ β-3 series.
Figure 4:
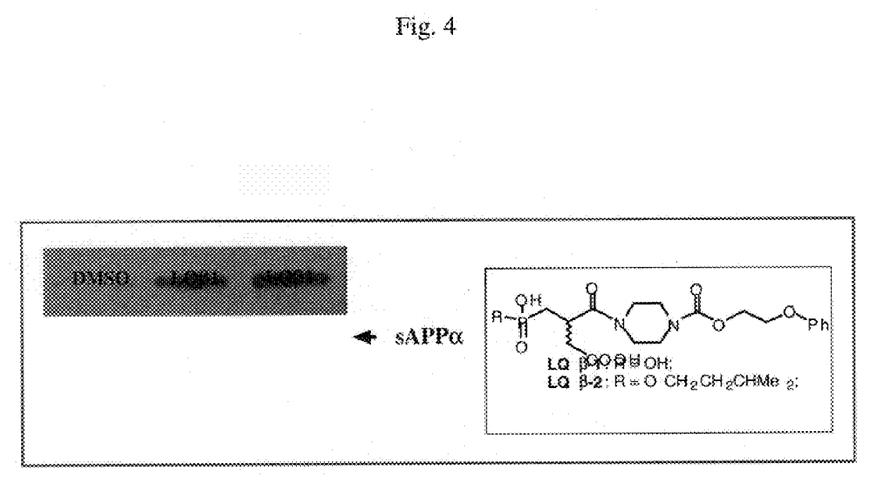
FIG. 4 depicts the effects of LQ-∃1 and LQ-∃2 series on sAPP secretion, both compounds at 10 μM have a marked effect of enhancing secretion compared to vehicle (DMSO) alone; inset depicts the chemical structure.
Figure 5:
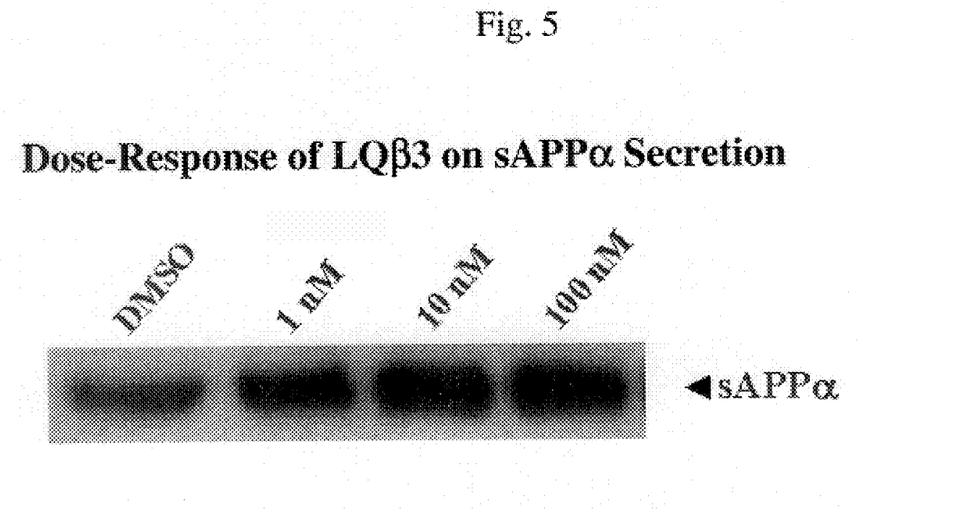
FIG. 5 depicts the dose dependent response of the LQ-β3 series on sAPP secretion, with noticeable effects starting at 1 nM and progressively increasing.

For the intermediates that are sensitive to strong reaction conditions like the additive $ME_3AL$, an alternative synthetic route can be applied. This methods is exemplified in FIG. 3 for the synthesis of LQ-β4 and LQ-β5 derivatives of the LQ-β3 series. Derivatives LQ-β4 and LQ-β5 were synthesized to optimize the C-terminal of the designed inhibitors. Itaconate (12) was prepared via the condensation of monobenzyl itaconate (7) with ortho-nitrophenol in the presence of DCC. Conjugate addition furnished the phosphinylmethyl moiety as N-terminus mimic. Nucleophilic substitution of ortho-nirophenol in compound (13) took place when it was treated with peptide (14). Final hydrogenolysis of the benzyl groups in compound (15) delivered the desired LQ-β4 and LQ-β5 derivatives.

Analysis of LQ-β1 to LQ-β5

LQ-β1

$^1$H NMR (300 MHz, DMSO-$d_6$) δ7.30 (d, 1H, J=6.9 Hz), 7.28 (d, 1H, J=7.2 Hz), 6.96 (d,2H, J=8.1 Hz), 6.94 (t, 1H, J=8.1 Hz), 4.34 (br t, 2H, J=4.5Hz), 4.20 (br t, 2H, J=4.5 Hz), 3.60–3.25 (m, 8H), 2.75–2.60 (m, 2H), 1.80–1.50 (m, 3H); $^{31}$P NMR (121 MHz, DMSO-$d_6$) δ24.12 ppm.

LQ-β2

$^1$H NMR (300 MHz, DMSO-$d_6$) δ7.28 (br t, 2H, J=8.7 Hz), 7.27 (br d, 1H, J=8.7 Hz), 4.34 (br t, 2H, J=4.5 Hz), 4.20 (br t, 2H, J=4.5 Hz), 3.85 (br q, 2H, J=6.6 Hz), 3.60–3.22 (m, 8H), 2.60 (br d, 2H, J=6.6 Hz), 1.80–1.60 (m, 3H), 1.45 (m, 2H), 0.86 (d, 6H, J=6.6 Hz); $^{31}$P NMR (121 MHz, DMSO-$d_6$) δ26.31 ppm.

LQ-β3

$^1$H NMR (300 MHz, DMSO-$d_6$) δ7.30 (d, 1H, J=7.2 Hz), 7.27 (d, 1H, J=7.2 Hz), 4.34 (br t, 2H, J=4.5 Hz), 4.19 (br t, 2H, J=4.5 Hz), 3.60–3.22 (m, 8H), 2.60 (br d, 2H, J=6.6 Hz)), 1.80–1.60 (m, 3H), 1.45 (m, 2H), 0.86 (d, 6H, J=6.6 Hz); $^{31}$P NMR (121 MHz, DMSO-$d_6$) δ-35.76 ppm.

LQ-β4

$^1$H NMR (300 MHz, DMSO-$d_6$) δ8.50 (d, 1H, J=8.1 Hz), 8.37 (d, 1H, J=7.2 Hz), 8.04 d, 1H, J=6.9 Hz), 7.28–7.18 (m, 5H), 4.37 (q, 1H, J=7.8 Hz), 4.17 (m, 2H), 3.40 (br m, 9H, active H), 3.08–2.90 (m, 3H), 2.43 (m, 1H)2.30–2.00 (m, 3H), 2.00–1.60 (m, 8H), 1.35 (s, 3H), 1.21 (d, 3H, J=7.2 Hz), 0.85 (d, 6H, J=6.6 Hz); with $D_2O$ exchange, δ8.37 and δ3.40 disappeared, while δ8.50 shift upfield, and δ8.04 shift downfield. $^{31}$P NMR (121 MHz, DMSO-$d_6$) δ-33.21 ppm.

LQ-β5

$^1$H NMR (300 MHz, DMSO-$d_6$) δ8.46 (d, 1H, J=8.4 Hz), 8.40 (d, 1H, J=6.6 Hz), 8.12 d, 1H, J=7.2 Hz), 7.29–7.19 (m, 5H), 4.77 (m, 1H), 4.37 (q, 1H, J=4.8 Hz), 4.17 (m, 2H), 3.40 (br m, 6H, active H), 3.08–2.90 (m, 3H), 2.96 (d, 2H, J=7.2 Hz), 2.45 (m, 1H)2.30–2.00 (m, 2H), 2.00–1.60 (m, 8H), 1.35 (s, 3H), 1.21 (d, 3H, J=7.2 Hz),0.99 (d, 3H, J=6.0 Hz), 0.85 (d, 6H, J=6.3 Hz); with $D_2O$ exchange, δ8.46 and δ3.40 disappeared, while δ8.40 shift upfield, and δ8.12 shift downfield. $^{31}$p NMR (121 MHz, DMSO-$d_6$) δ-32.91 ppm.

Biological Activity

Determination of the enhancement of sAPP secretion promoted by LQ-β series of compounds:

Cells and Cell Culture Procedures:

Human fibroblasts were obtained from the Coriell Cell Repositories (Camden, N.J.). Four AD cell lines (AG06848, AG04401, AG07377, AG06263) and four age-matched control cell lines (AG07141, AG06241, AG08044, AG04560) were grown to confluence in T75 cell culture flasks. Additional information about these cell lines can be found in the Catalog of Cell Lines from the National Institute of Aging. (National Institute of Aging, Catalog of Cell Lines (1994)). The culture medium was DMEM supplemented with 10% serum (FBS, Gibco). PC12 cells were obtained from the American Cell Culture Collection and grown to confluence in T75 flasks containing DMEM supplemented with 5% FBS (Gibco), 10% horse serum (Biofluids) and 1% of a mixture of penicillin (5,000 units/ml in G sodium) and streptomycin (5,000 μg/ml).

sAPP Secretion:

Cells in T-75 were seeded into 100 mm cell culture plates and allowed to grow for 2 days. Complete culture medium was removed and replaced by serum free medium 2 hours before drug treatment. Cells were treated for 2 hours with LQ-β series (1 nM and 10 nM, 100 nM and 20 μM), LQ-βseries and DMSO alone. After 2 hours of incubation, the supernatant was removed and the secreted proteins were precipitated with 10% TCA and resuspended in TrisGlycine SDS electrophoresis sample buffer. The samples were boiled for 5 minutes, subjected to electrophoresis and later immunoblotting for identification of sAPP.

Measurement of Secreted APPα; (sAPPα):

Conventional immunoblotting techniques were employed. (Dumbar, G. S., *Protein Blotting—A Practical*

Approach. Oxford: Oxford University Press, 1994). Such techniques are known in the art are described in *Protein Blotting—A Practical Approach* by Dumbar. Precipitated protein extracts from each cell line and condition were loaded to freshly prepared 10% acrylamide Tris-HCl mini-gels and separated by SDSPAGE. The volume of sample loaded was corrected for total cell protein per dish. Proteins were transferred electrophoretically to PVDF membranes. The membranes were saturated with 5% non-fat dry milk to block non-specific binding. Blocked membranes were incubated overnight at 4° C. with 1:500 6E10 monoclonal antibody specific for sAPP (SENETEK). (Kim, K. S., et al., 7 *Neurosci Res. Commun.* 113–22, 1990). After washing, the membranes were incubated for 1 hour at room temperature with horseradish peroxidase conjugated anti-mouse IgG secondary antibody (Jackson's Laboratories). Horseradish peroxidase bound signal was detected using an enhanced chemiluminescence followed by exposure to Hyperfilm ECL (Amersham). The band intensities were quantified by densitometric analyses using a BioRad GS-710 Scanning Densitometer and Multianalyst software (BioRad).

While the invention has been described in terms of various preferred embodiments, those skilled in the art will recognize that various modifications, substitutions, omissions, and changes can be made without departing from the spirit of the invention. Accordingly, it is intended that the scope of the invention be limited solely by the scope of the following claims.

What is claimed is:

1. A compound that comprises a phosphorylmethyl succinic acid that is 4-(2-Carboxymethyl-3-phosphono-propionyl)-piperazine-1-carboxylic acid 2-phenoxy-ethyl ester or a salt or hydrate thereof.

2. The compound comprising a phosphorylmethyl succinic acid that is 4-{2-Carboxymethyl-3- [hydroxy-(3-methyl-butoxy)-phosphoryl]-propionyl}-piperazine-1-carboxylic acid 2-phenoxy-ethyl ester or a salt or hydrate thereof.

3. A compound comprising a phosphinylmethyl succinic acid that is 4-{2-Carboxymethyl-3-[hydroxy-(3-methyl-butyl)-phosphinoyl]-propionyl}-piperazine-1-carboxylic acid 2-phenoxy-ethyl ester or a salt or hydrate thereof.

4. A compound comprising a phosphinylmethyl succinic acid that is 3-{1-[3-Carboxy-1-(1-carboxy-2-phenyl-ethylcarbamoyl)-propylcarbamoyl]-ethylcarbamoyl}-4-[hydroxy-(3-methyl-butyl)-phosphinoyl]-butyric acid or a salt or hydrate thereof.

5. A compound comprising a phosphinylmethyl succinic acid that is 3-{1-[3-Carboxy-1-(1-isopropoxycarbonyl-2-phenyl-ethylcarbamoyl)-propylcarbamoyl]-ethylcarbamoyl}-4-[hydroxy-(3-methyl-butyl)-phosphinoyl]-butyric acid or a salt or hydrate thereof.

6. A composition comprising a mixture of at least two of said phosphorylmethyl and/or phosphinylmethyl succinic and/or glutaric acid compounds and wherein said composition regulates the processing of APP wherein said phosphorylmethyl and/or phosphinylmethyl succinic and/or glutaric acid compounds are of a formula (I):

or salts or hydrates thereof;
wherein n is 1 or 2;
wherein X is a phosphinylmethyl or phosphorylmethyl of a formula (II):

wherein $R_1$ is H, OH, R, OR, SR, $N(R)_2$, $(CH_2)_mC(O)R$, $(CH_2)_mCOOR$, $(CH_2)_mP(O)(OR)_2$, $(CH_2)_mS(O)R$, or $(CH_2)_mSO_2R$; wherein each R is independently H, $(C_1-C_{22})$alkyl, $(C_6-C_{10})$aryl, $(C_3-C_8)$cycloalkyl, $(C_2-C_{22})$alkenyl, $(C_5-C_8)$cycloalkenyl, $(C_7-C_{32})$aralkyl, $(C_7-C_{32})$alkylaryl, $(C_9-C_{32})$aralkenyl, or $(C_9-C_{32})$alkenylaryl; and where m is 1 to 5;

wherein $R_2$ is H, R, OR, SR, $N(R)_2$, $(CH_2)_mC(O)R$, $(CH_2)_mCOOR$, $(CH_2)_mP(O)(OR)_2$, $(CH_2)_mS(O)R$, or $(CH_2)_mSO_2R$ with the proviso that $R_2$ is not OH;

wherein each R is independently H, $(C_1-C_{22})$alkyl, $(C_2-C_{22})$alkenyl, or a heterocycle, where m is 1 to 5.

7. A composition comprising a mixture of at least two phosphorylmethyl and/or phosphinylmethyl succinic and/or glutaric acid compounds and wherein said composition regulates the processing of APP wherein said phosphorylmethyl and/or phosphinylmethyl succinic and/or glutaric acid compounds are selected from 4-(2-Carboxymethyl-3-phosphono-propionyl)-piperazine-1-carboxylic acid 2-phenoxy-ethyl ester or a salt or hydrate thereof, 4-{2-Carboxymethyl-3-[hydroxy-(3-methyl-butoxy)-phosphoryl]-propionyl}-1-piperazine-1-carboxylic acid 2-phenoxy-ethyl ester or a salt or hydrate thereof, 4-{2-Carboxymethyl-3-[hydroxy-(3-methyl-butyl)-phosphinoyl]-propionyl}-1-piperazine-1-carboxylic acid 2-phenoxy-ethyl ester or a salt or hydrate thereof, 3-{1-[3-Carboxy-1-(1-carboxy-2-phenyl-ethylcarbamoyl)-propylcarbamoyl]-ethylcarbamoyl}-4-[hydroxy-(3-methyl-butyl)-phosphinoyl]-butyric acid or a salt or hydrate thereof, or 3-{1-[3-Carboxy-1-(1-isopropoxycarbonyl-2-phenyl-ethylcarbamoyl)-propylcarbamoyl]-ethylcarbamoyl}-4-[hydroxy-(3-methyl-butyl)-phosphinoyl]-butyric acid or a salt or hydrate thereof.

8. A composition comprising a mixture of at least two phosphorylmethyl and/or phosphinylmethyl succinic and/or glutaric acid compounds and wherein said composition regulates the processing of APP wherein said phosphorylmethyl and/or phosphinylmethyl succinic and/or glutaric acid compounds are of a formula (I):

or salts or hydrates thereof;
wherein n is 1 or 2;
wherein X is a phosphinylmethyl or phosphorylmethyl of a formula (II):

wherein $R_1$ is H, OH, R, OR, SR; wherein each R is independently H, $(C_1-C_{22})$alkyl;

wherein $R_2$ is H, R, OR, SR, $N(R)_2$ with the proviso that $R_2$ is not OH;

wherein each R is independently H, $(C_1-C_{22})$alkyl.

* * * * *

UNITED STATES PATENT AND TRADEMARK OFFICE
CERTIFICATE OF CORRECTION

PATENT NO. : 6,562,783 B2
DATED : May 13, 2003
INVENTOR(S) : Lixin Qiao and Rene Etcheberrigaray It is certified that error appears in the above-identified patent and that said Letters Patent is hereby corrected as shown below:

<u>Title page, Item [54] and Column 1, line 4,</u>
Replace "GLUTAURIC" with -- GLUTARIC --

<u>Title page,</u>
Item [73], replace "Neurologic" with -- NeuroLogic --

Signed and Sealed this

Twenty-sixth Day of August, 2003

JAMES E. ROGAN
*Director of the United States Patent and Trademark Office*